United States Patent
Maes et al.

(10) Patent No.: US 6,867,021 B2
(45) Date of Patent: Mar. 15, 2005

(54) **MULTIPLEX RT-PCR/PCR FOR SIMULTANEOUS DETECTION OF BOVINE CORONAVIRUS, BOVINE ROTAVIRUS, *CRYPTOSPORIDIUM PARVUM*, AND *ESCHERICHIA COLI***

(75) Inventors: Roger K. Maes, Okemos, MI (US); Annabel G. Wise, Bath, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 449 days.

(21) Appl. No.: 09/789,084

(22) Filed: Feb. 20, 2001

(65) Prior Publication Data

US 2005/0026144 A1 Feb. 3, 2005

(51) Int. Cl.[7] .......................... C12P 19/34; C07H 21/04
(52) U.S. Cl. ...................... 435/91.2; 435/6; 435/91.1; 435/91.51; 536/23.1; 536/23.7; 536/23.72; 536/24.3; 536/24.33
(58) Field of Search .................. 435/6, 91.1, 91.2, 435/91.51; 536/23.1, 23.7, 23.72, 24.3, 24.33, 24.1

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,234,809 A | 8/1993 | Boom et al. |
| 5,298,392 A | 3/1994 | Atlas et al. |
| 5,437,990 A | 8/1995 | Burg et al. |
| 5,716,784 A | 2/1998 | Di Cesare |
| 5,756,701 A | 5/1998 | Wu et al. |
| 5,770,368 A | 6/1998 | De Leon et al. |
| 5,866,336 A | 2/1999 | Nazarenko et al. |
| 5,882,856 A | 3/1999 | Shuber |
| 5,959,093 A | 9/1999 | Saif et al. |

OTHER PUBLICATIONS

Thorns et al. (Am. J. Vet. Res. (1992) 53(1): 36–43).*
Elnifro et al. (Clin. Microbiol. Rev. (2000) 13(4): 559–570).*
Naciri et al. (Vet. Parasitol. (1999) 85(4): 245–257).*
Grondahl et al. (J. Clin. Microbiol. (1999) 37(1): 1–7).*
Cubbon et al. (J Med Microbiol. (1996) 44(3) 219–222).*
Edwards et al. (PCR Methods and Applications (1994) 3(4): S65–S75.*
Blanco et al., J. Clin. Microbiol. 35: 2958–2963 (1997).
Franck et al., J. Clin. Microbiol. 36: 1795–1797 (1998).
Qiagen Dneasy Tissue Kit Handbook protocol (Qiagen, Inc., Apr. 1999 Edition, pp. 16–18.
Balatbat et al., J. Clin. Microbiol. 34: 1769–1772 (1996).
Tsunemitsu et al., Arch. Virol. 144: 167–175 (1999).
Heid et al., Genome Res. 6: 986–994 (1996).
Mainil, J.G. et al, American Journal of Veterinary Research, vol. 51, No. 2, pp. 187–190 (1990).

* cited by examiner

Primary Examiner—Carla J. Myers
Assistant Examiner—Alexander H. Spiegler
(74) Attorney, Agent, or Firm—Ian C. McLeod

(57) ABSTRACT

The present invention provides a multiplex RT-PCR/PCR method, which enables in a single assay the simultaneous detection of any combination of bovine rotavirus, bovine coronavirus, *Cryptosporidium parvum*, and optionally, *Escherichia coli* strains producing K99 pili or heat-stable enterotoxin STa.

10 Claims, 2 Drawing Sheets

MULTIPLEX RT-PCR/PCR FOR SIMULTANEOUS DETECTION OF BOVINE CORONAVIRUS, BOVINE ROTAVIRUS, *CRYPTOSPORIDIUM PARVUM*, AND *ESCHERICHIA COLI*

CROSS-REFERENCE TO RELATED APPLICATION

Not applicable.

STATEMENT REGARDING FEDERALLY SPONSORED RESEARCH OR DEVELOPMENT

Not applicable.

BACKGROUND OF THE INVENTION

(1) Field of the Invention

The present invention relates to a multiplex RT-PCR/PCR method, which enables in a single assay the simultaneous detection of any combination of bovine rotavirus, bovine coronavirus, *Cryptosporidium parvum*, and optionally, *Escherichia coli* strains producing K99 pili and heat-stable enterotoxin STa or STb.

(2) Description of Related Art

In the United States, bovine rotavirus, bovine coronavirus, *Cryptosporidium parvum*, and *Escherichia coli* strains producing K99 pili or fimbriae or heat-stable enterotoxin STa are the five most common infectious agents in neonatal calf diarrhea, commonly referred to as scours. The relative incidence of these pathogens in a multi-state survey of causes of scours in beef cattle was 35% for rotavirus and coronavirus combined, 24% for *Cryptosporidium parvum*, 22% for *Escherichia coli*, and 19% for others. The percent involvement in a study of scours in dairy calves was 46% for rotavirus, 15% for coronavirus, 23% for *Cryptosporidium parvum*, 13% for *Salmonella* spp., and 3% for *Escherichia coli*. Identification of these pathogens is a time consuming and laborious process.

For detecting bovine rotavirus and bovine coronavirus, electron microscopy or antigen-detection ELISA have been the standard detection method. Virus isolation is an attempt to isolate the virus in cell culture and then characterizing the isolated virus by standard virological methods. Other methods for detecting bovine rotavirus and bovine coronavirus include demonstrating the presence of rotavirus particles by negative staining electron microscopy, detecting rotavirus or coronavirus antigens by an antigen-detection enzyme linked immunosorbant assay (ELISA), or detection of the rotavirus or coronavirus RNA genome reverse transcription-polymerase chain reaction (RT-PCR) assays. For example, U.S. Pat. No. 5,959,093 to Saif et al. provides nucleic acid sequences encoding the VP4 and VP7 proteins from several bovine rotavirus serotypes and discloses a PCR method and primers for isolating cDNA encoding VP6.

*Cryptosporidium parvum* is detected by light microscopic examination of fecal smears for oocysts or by PCR of fecal samples using *Cryptosporidium parvum* specific oligonucleotide primers. For example, U.S. Pat. No. 5,770,368 to De Leon et al. discloses a method for detecting encysted forms of *Cryptosporidium* that are viable and infectious. The method involves isolating oocysts, inducing transcription of the heat shock protein (HSP) genes, and detecting the induced transcripts by RT-PCR. Alternatively, infectivity is determined by cultivating the *Cryptosporidium* on susceptible cells and either amplifying HSP DNA from infected cells by PCR or induce HSP transcription and detecting the induced transcripts by RT-PCR.

*Escherichia coli* producing K99 pili are detected by culturing fecal samples in specialized media and demonstrating the presence of K99 pili by immunological methods or by PCR using oligonucleotide primers specific to *Escherichia coli* strains producing K99 pili or heat-stable enterotoxin STa (Franck et al., J. Clin. Microbiol. 36: 1795–1797 (1998).

PCR is generally considered the most sensitive and rapid method for detecting nucleic acids of a pathogen in a particular sample. PCR is well known in the art and has been described in U.S. Pat. No. 4,683,195 to Mullis et al., U.S. Pat. No. 4,683,202 to Mullis, U.S. Pat. No. 5,298,392 to Atlas et al., and U.S. Pat. No. 5,437,990 to Burg et al. In the PCR step, oligonucleotide primer pairs for each of the target pathogens are provided wherein each primer pair comprises a first nucleotide sequence complementary to a sequence flanking the 5' end of the target nucleic acid sequence and a second nucleotide sequence complementary to a nucleotide sequence flanking the 3' end of the target nucleic acid sequence. The nucleotide sequences comprising each oligonucleotide primer pair are specific to particular pathogen to be detected and do not cross-react with other pathogens.

Multiple infectious agents are frequently involved in outbreaks of neonatal calf diarrhea. Thus, diarrhea in neonatal calves can be the result of infection by one or more of bovine rotavirus, bovine coronavirus, *Cryptosporidium parvum*, and *Escherichia coli* producing K99 pili or heat-stable enterotoxin STa. However, currently used assays have severe limitations in detecting these agents. Virus isolation and bacterial culture methods are labor intensive and costly and can involve days or weeks of culturing. Electron microscopy is also labor intensive and also is of limited sensitivity. ELISA is also a time consuming method. However, the primary drawback of ELISA is that it can result in false negatives when antigen-antibody complexes are shed instead of free virus particles and ELISA has limited sensitivity. None of the above methods are suitable for the simultaneous detection of multiple pathogens in a sample. PCR is a sensitive and rapid method for detecting pathogens, and it is amenable to simultaneously detecting multiple pathogens in a sample; however, using PCR for the simultaneous detection of multiple pathogens in a sample has been problematic. The primary obstacles to simultaneous detection of multiple pathogens have been cross-reactivity and preferential amplification of particular target sequences in the sample at the expense of the other target sequences in the sample. While U.S. Pat. No. 5,756,701 to Wu et al. discloses a multiplex PCR method for simultaneously detecting *Salmonella* spp., *Yersinia* spp., and *Escherichia coli* in a sample, the method is specific for the aforementioned bacterial species and does not include RT-PCR for detecting RNA viruses. U.S. Pat. No. 5,882,856 to Shuber also discloses a multiplex PCR method; however, the method uses chimeric primers comprising a sequence complementary to the target sequence covalently linked to a non-complementary sequence. Franck et al., J. Clin. Microbiol. 36: 1795–1797 (1998), discloses a multiplex PCR method for detecting particular *Escherichia coli* strains that encode K99 pili or heat-stable enterotoxin STa. However, the method does not include RT-PCR for detecting RNA viruses. In general, because of the difficulty in developing PCR methods, particularly RT-PCR methods, that enable simultaneous detection of multiple pathogens in a sample, most samples to be analyzed by PCR for multiple pathogens, are separately tested for each of the multiple pathogens in separate PCR reactions.

Because current methods for detecting the four most important infectious agents in neonatal calf diarrhea requires performing four separate assays, there is a need for a method which would enable the simultaneous detection of the four most important infectious agents involved in neonatal calf diarrhea. Simultaneous detection would provide substantial savings in cost and time in determining which of the four infectious agents is involved in a particular outbreak of neonatal calf diarrhea. Because simultaneous detection of any combination of these four agents in a single assay would avoid the potential for overlooking dual or even triple infections, the appropriate therapy could be initiated in a more timely and effective manner.

SUMMARY OF THE INVENTION

The present invention provides a multiplex RT-PCR/PCR assay which enables in a single assay the simultaneous detection of bovine rotavirus, bovine coronavirus, *Cryptosporidium parvum*, and *Escherichia coli* strains producing K99 pili or heat-stable enterotoxin STa or STb. The present invention has the advantage over the prior art in that it can detect any combination of bovine rotavirus, bovine coronavirus, *Cryptosporidium parvum*, or *Escherichia coli* strains producing K99 pili or heat-stable enterotoxin STa or STb in a single assay which is rapid, sensitive, and specific.

Thus, the present invention provides a method of screening to simultaneously detect at least two pathogens selected from the group consisting of bovine coronavirus, bovine rotavirus, and *cryptosporidium parvum* in a fecal sample, the method comprising: (a) isolating nucleic acids consisting of RNA and DNA from the fecal sample; (b) providing in an RT-PCR/PCR reaction mixture the nucleic acids, at least two primer pairs selected from the group consisting of a first oligonucleotide primer pair which hybridizes to opposite strands of a target nucleic acid sequence of *Cryptosporidium parvum*, a second oligonucleotide primer pair which hybridizes to opposite strands of a target nucleic acid sequence of bovine coronavirus, and a third oligonucleotide primer pair which hybridizes to opposite strands of a target nucleic acid sequence of bovine rotavirus, wherein each primer pair flanks its target nucleic acid sequence for PCR amplification of the target nucleic acid sequence, four deoxynucleotide triphosphates selected from the group consisting of adenosine deoxynucleotide triphosphate, guanosine deoxynucleotide triphosphate, thymidine deoxynucleotide triphosphate, cytosine deoxynucleotide triphosphate, and nucleotide analogs thereof, a thermostable DNA polymerase, and a reverse transcriptase; (c) synthesizing a target cDNA of the RNA comprising the nucleic acids under suitable reverse transcription reaction conditions with the deoxynucleotide triphosphates and reverse transcriptase; (d) amplifying the target DNA and cDNA in the reaction mixture under suitable PCR reaction mixture temperature conditions by a repetitive series of PCR thermal cycling steps comprising: (1) denaturing the target DNA and cDNA into opposite strands; (2) hybridizing the oligonucleotide primers to the appropriate denatured strands, and (3) extending the hybridized primers with the four deoxynucleotide triphosphates and the nucleic acid polymerase; and (c) following amplification of the target nucleic acid sequence by one or more series of the thermal cycling steps, screening for the amplified PCR products. Preferably, in the method of the cDNA synthesis, the cDNA is synthesized from the RNA in a reaction at about 50° C. for about 30 minutes followed by predenaturation at 95° C. for 15 minutes. The PCR reaction is for 44 cycles wherein each cycle consists of denaturing the DNA at about 94° C. for about 30 seconds, annealing the primers to the denatured DNA at about 55° C. for about 30 seconds, and extending the primers at about 72° C. for about 1 minute.

In a preferred embodiment of the method, the first primer pair comprises an upstream primer with the sequence in SEQ ID NO:1 and a downstream primer with the sequence in SEQ ID NO:2, the second primer pair comprises the upstream primer with the sequence in SEQ ID NO:3 and the downstream primer with the sequence in SEQ ID NO:4, and the third primer pair comprises the upstream primer with the sequence in SEQ ID NO:5 and the downstream primer with the sequence in SEQ ID NO:6. Optionally, the group of primer pairs further includes at least one additional oligonucleotide primer pair, which hybridizes to opposite strands of a target nucleic acid sequence of *Escherichia coli*, selected from the group of primer pairs consisting of an upstream primer that includes the nucleic acid sequence in SEQ ID NO:7 and a downstream primer that includes the nucleic acid sequence in SEQ ID NO:8 for detecting a target sequence encoding K99 pili, and an upstream primer that includes the nucleic acid sequence in SEQ ID NO:9 and a downstream primer that includes the nucleic acid sequence in SEQ ID NO:10 for detecting a target encoding heat-stable enterotoxin STa.

In the method, it is preferable that the reaction mixture comprise 0.6 $\mu$M each of the upstream primer and the downstream primer of the first primer pair (SEQ ID Nos: 1 and 2), 0.9 $\mu$M each of the upstream primer and the downstream primer of the second primer pair (SEQ ID Nos: 3 and 4), and 0.6 $\mu$M each of the upstream primer and the downstream primer of the third primer pair (SEQ ID NO: 5 and 6).

In a particular embodiment of the method, the sample comprises the bovine coronavirus, bovine rotavirus, *Cryptosporidium parvum*, and *Escherichia coli*, which are isolated from the fecal sample by immunomagnetic separation.

The present invention further provides a kit for simultaneous screening of a fecal sample for at least two pathogens selected from the group consisting of bovine coronavirus, bovine rotavirus, and *Cryptosporidium parvum* comprising in three or more containers: (a) a first oligonucleotide primer pair which hybridizes to opposite strands of a target nucleic acid sequence of *Cryptosporidium parvum*; (b) a second oligonucleotide primer pair which hybridizes to opposite strands of a target nucleic acid sequence of bovine coronavirus; and (c) a third oligonucleotide primer pair which hybridizes to opposite strands of a target nucleic acid sequence of bovine rotavirus, wherein each primer pair flanks its target nucleic acid sequence for PCR amplification of the target nucleic acid sequence.

In a preferred embodiment of the kit, the first primer pair comprises an upstream primer with the sequence in SEQ ID NO:1 and a downstream primer with the sequence in SEQ ID NO:2, the second primer pair comprises the upstream primer with the sequence in SEQ ID NO:3 and the downstream primer with the sequence in SEQ ID NO:4, and the third primer pair comprises the upstream primer with the sequence in SEQ ID NO:5 and the downstream primer with the sequence in SEQ ID NO: 6. Optionally, the kit further includes at least one additional oligonucleotide primer pair, which hybridizes to opposite strands of a target nucleic acid sequence of *Escherichia coli*, selected from the group consisting of an upstream primer that includes the nucleic acid sequence in SEQ ID NO:7 and a downstream primer that includes the nucleic acid sequence in SEQ ID NO:8 for detecting a target sequence encoding K99 pili, and an upstream primer that includes the nucleic acid sequence in SEQ ID NO:9 and a downstream primer that includes the nucleic acid sequence in SEQ ID NO:10 for detecting a target encoding heat-stable enterotoxin STa.

In a particular embodiment, the kit further comprises in one or more containers at least one of an optimized buffer for the reaction, a positive control nucleic acid comprising the target nucleic acid sequence, a mixture of deoxynucleotide triphosphates comprising adenosine deoxynucleotide triphosphate, guanosine deoxynucleotide triphosphate, thymidine deoxynucleotide triphosphate, cytosine deoxynucleotide triphosphate, and nucleotide analogs thereof, a thermostable DNA polymerase, and a reverse transcriptase. In a particular embodiment, the kit further includes a container comprising immunomagnetic beads, which enable immunomagnetic separation of bovine coronavirus, bovine rotavirus, *Cryptosporidium parvum*, and *Escherichia coli* from the fecal sample.

For either the method or the kit, the present invention can further include one or more nucleic acid probes for detecting the amplified PCR product wherein each probe is complementary to a sequence within the target sequence of one of the pathogens. In a particular embodiment, the probes are labeled at its 5' end with an energy transfer donor fluorophore and labeled at its 3' end with an energy transfer acceptor fluorophore. Preferably, the fluorophore is selected from the group consisting of fluorescein, 5-carboxyfluorescein (FAM), 2'7'-dimethoxy-4',5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), tetrachloro-6-carboxy-fluorescein (TET), VIC, and 5-(2'-aminoethyl)aminonaphthalene-1-sulfonic acid (EDANS). Preferably, the probes are blocked against chain extension at their 3' ends.

OBJECTS

Therefore, it is an object of the present invention to provide a multiplex PCR test which allows the rapid, sensitive, and specific detection of bovine rotavirus, bovine coronavirus, *Cryptosporidium parvum*, and K99 *Escherichia coli* in a single assay.

These and other objects of the present invention will become increasingly apparent with reference to the following drawings and preferred embodiments.

DETAILED DESCRIPTION OF THE INVENTION

Figure 1:
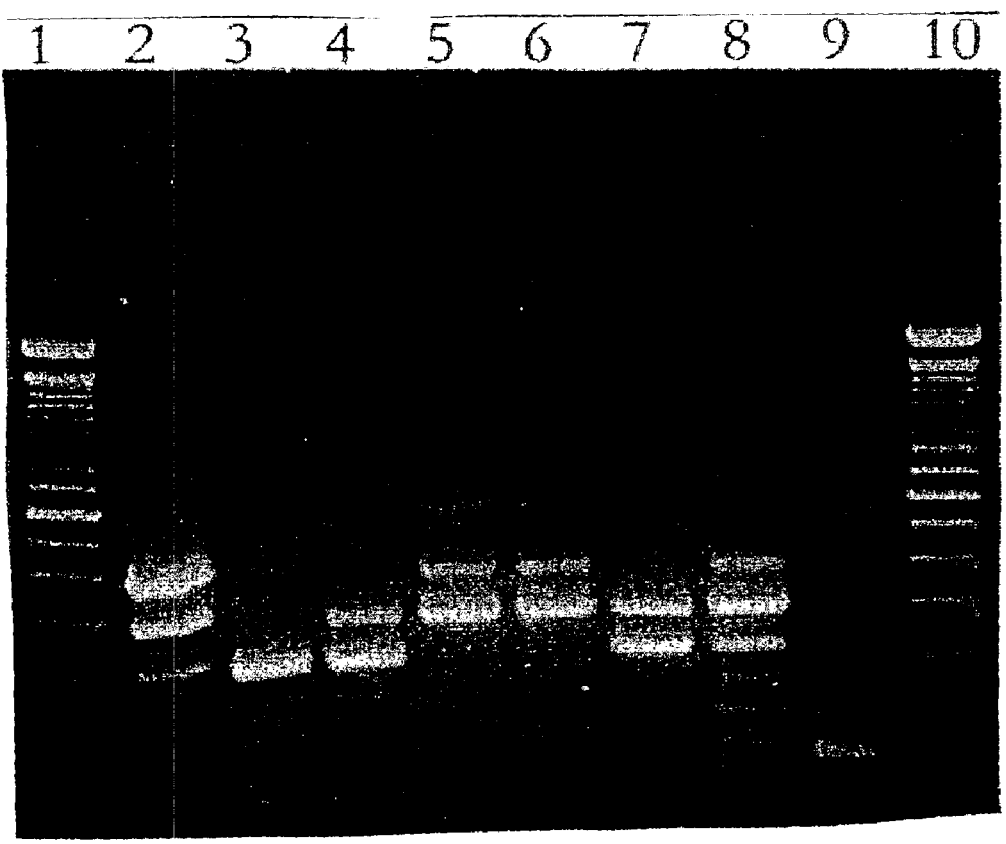
FIG. 1 shows the PCR amplification products resolved on an ethidium bromide stained 2% agarose gel following the multiplex RT-PCR/PCR reaction of the present invention on nucleic acids extracted from fecal samples submitted to the Animal Health Diagnostic Laboratory at Michigan State University. Lanes 1 and 10 show a 100 base-pair (bp) DNA ladder. Lane 2 shows a positive control from reference strains of bovine coronavirus, bovine rotavirus, and *Cryptosporidium parvum* showing the 406 bp, 294 bp, and 194 bp PCR products, respectively. Lane 9 shows a negative control using water as the template. Lanes 3–8 show the PCR products obtained from the submitted fecal samples.

All patents, patent applications, and literature references cited in this specification are hereby incorporated herein by reference in their entirety. In case of conflict, the present description, including definitions, will control.

The term "amplification" of DNA as used herein means the use of polymerase chain reaction (PCR) to increase the concentration of a particular DNA sequence within a mixture of DNA sequences. The particular DNA sequence that is amplified is a "target" sequence.

The term "primer pair" means a pair of oligonucleotide primers which are complementary to the sequences which flank the target sequence. The primer pair consists of an upstream primer which has a nucleic acid sequence that is complementary to a sequence upstream of the target sequence and a downstream primer which has a nucleic acid sequence that is complementary to a sequence downstream of the target sequence.

The term "reverse transcription" as used herein means a method wherein a cDNA copy of an RNA molecule is made in a method called "reverse transcription" (RT). The cDNA product can be used as a template for PCR.

The term "RT-PCR" as used herein means a reaction wherein an RNA molecule is reversed transcribed to make a cDNA product and the cDNA product is subsequently amplified in a PCR reaction. Typically, both the reverse transcription and the PCR reactions of the RT-PCR reaction are performed in a single tube.

The term "multiplex PCR" as used herein means the simultaneous PCR amplification of multiple DNA target sequences in a single mixture.

The term "multiplex RT-PCR/PCR" as used herein means reverse transcribing the multiple RNA molecules in a sample that contains a mixture of RNA and DNA molecules to produce a mixture that contains multiple cDNA and DNA molecules, and then simultaneously PCR amplifying particular target sequences from the multiple cDNA and DNA molecules in a single reaction mixture.

The present invention provides a multiplex RT-PCR/PCR method for detecting bovine coronavirus, bovine rotavirus, *Cryptosporidium parvum*, and *Escherichia coli* producing K99 pili or fimbriae, or heat-stable enterotoxin STa or STb in the feces of cattle, particularly feces of neonatal calves. The present invention combines in a single assay a reverse transcription (RT) step to make cDNA copies of the RNA virus genomes and a multiplex PCR step to amplify the appropriate target sequences in the viral cDNA copies and the protozoal or bacterial DNA genomes.

The multiplex RT-PCR/PCR assay of the present invention enables a laboratory or practitioner to determine whether a fecal sample from a calf contains one or more of *Cryptosporidium parvum*, bovine coronavirus, bovine rotavirus, and *Escherichia coli* producing K99 pili or heat-stable enterotoxin STa or STb. Because the present invention enables the rapid identification of which of the above pathogens the calf is infected with, it enables the treatment of the calf to be tailored to the particular pathogens that have infected the calf instead of unilaterally treating the calf for infection by all three pathogens. This ability to tailor treatment saves time and costs, and can result in shortening the duration of infection by the above pathogens.

The multiplex RT-PCR/PCR assay uses in a single reaction, at least two primer pairs selected from the group consisting of a primer pair complementary to a particular region of the *Cryptosporidium parvum* genome, a primer pair complementary to a particular region of the bovine coronavirus genome, a primer pair complementary to a particular region of the bovine rotavirus genome, and a primer pair complementary to the region of the *Escherichia coli* genome that encodes K99 pili or heat-stable enterotoxin STa or STb.

In a preferred embodiment, the multiplex RT-PCR/PCR assay uses in a single reaction, at least two primer pairs selected from the group consisting of a primer pair comprising SEQ ID NOs: 1 and 2 to amplify a 194 bp region of the *Cryptosporidium parvum* genome, a primer pair comprising SEQ ID NOs: 3 and 4 to amplify a 406 bp region of the bovine coronavirus nucleocapsid gene, and a primer pair comprising SEQ ID NOs: 5 and 6 to amplify a 294 bp region of the group antigen (VP6) gene of bovine rotavirus. Optionally, at least one additional primer pair is included with the above primer pairs which targets a sequence within the gene encoding the K99 pili or the heat-stable enterotoxin STa. The primer pairs enable PCR amplification of the target sequence in *Escherichia coli* K99 or STa strains. The strain K99 primers are set forth in SEQ ID Nos: 7 and 8, and the strain STa primers are set forth in SEQ ID Nos: 9 and 10.

The primer pairs are provided in particular concentrations that reduce the occurrence of preferential amplification, a phenomenon that occurs in PCR reactions which attempt to simultaneously amplify multiple species of target nucleic acid sequences. Preferential amplification results in the disproportionate amplification of one or more target nucleic acid sequence species at the expense of the other target sequence species such that the amount of the preferentially amplified sequences greatly exceeds the amount of the other non-preferred sequences. The overproduction of amplified product for particular target sequence species causes the underproduction of amplified product for the other target sequence species. Thus, a particular target sequence species may not be detectable in a multiplex PCR reaction even though it is present in the reaction mixture. Preferential amplification occurs in part because different primers have different physical properties and, therefore, will have different amplification efficiencies under a particular simultaneous PCR condition. In addition to the physical characteristics of the primers, other reaction conditions such as magnesium concentration, DNA polymerase used, concentration of DNA polymerase, target sequence concentration, annealing temperature, and primer concentration also affect amplification efficiency of a particular target nucleic acid sequence. In addition, the source from which the target sequences are isolated, e.g., feces or urine, and the method for isolating the nucleic acids can also affect amplification of particular target sequences. Because of the large number of variables that need to be adjusted to enable the simultaneous amplification of multiple target nucleic acid sequence species, developing a multiplex PCR method is difficult and time consuming. Particularly, when the reaction must further include a preceding reverse transcription step to make the target nucleic acid sequence. In some cases, suitable PCR reaction conditions, which allow the simultaneous amplification of all the target sequence species in the reaction mixture, have remained elusive. Therefore, many investigators find it preferable to perform multiple PCR reactions, wherein each PCR reaction separately detects one of the multiple target nucleic acid sequences in a sample, than to discover the proper conditions for simultaneously detecting the multiple target nucleic acid sequences in a single reaction.

A multiplex RT-PCR/PCR method for detecting bovine rotavirus, bovine coronavirus, and *Cryptosporidium parvum* would have been particularly difficult to develop because each pathogen has a nucleic acid template of a particular type: bovine rotavirus has a double-stranded RNA genome, bovine coronavirus has a single-stranded RNA genome, and *Cryptosporidium parvum* and *Escherichia coli* have large DNA genomes. Thus, a multiplex RT-PCR/PCR method, in addition to adjusting reaction parameters that compensate for differences in sequence content for each of the genomes, must also incorporate steps which are specific for each particular nucleic acid type, i.e., a cDNA synthesis step to copy the viral RNA genomes, a denaturation step to enable a cDNA copy to made from the bovine rotavirus genome, and a PCR step that efficiently copies the cDNA copies and the bacterial DNA genome. Thus, development of a functional multiplex PCR method involves significant trial and error and for particular cases, functional multiplex PCR methods has not been achievable.

However, despite the differences between the nucleic acid genomes of bovine coronavirus, bovine rotavirus, and *Cryptosporidium parvum*, a multiplex RT-PCR/PCR reaction was developed that allowed the simultaneous amplification and detection of bovine rotavirus, bovine coronavirus, *Cryptosporidium parvum*, and *Escherichia coli*. Since the multiplex RT-PCR/PCR method herein shows that a single reaction can be used to detect such different nucleic acid genomes it would now be obvious to one skilled in the art that other primer pairs can be selected which are as effective as the primer pairs disclosed herein. Therefore, it is within the scope of the present invention to include primer pairs, other than those disclosed herein, which are complementary to other regions of the genomes of bovine coronavirus, bovine rotavirus, *Cryptosporidium parvum*, and *Escherichia coli* producing K99 pili or heat-stable enterotoxin STa or STb.

To perform the multiplex RT-PCR/PCR assay of the present invention, nucleic acids are isolated from a fecal sample according to methods well known in the art. In a preferred isolation method, which uses a modification of the Qiagen DNEASY Tissue Kit Handbook protocol (Qiagen, Inc., April 1999 Edition, pp. 16–18, Valencia, Calif.), about 20 to 30 mg of feces is resuspended in 180 $\mu$l ATL buffer (Qiagen, Inc.). This protocol is based upon U.S. Pat. No. 5,234,809 to Boom et al. To lyse the cells and viruses in the suspension, of proteinase K is added in an amount to digest the proteins in the suspension (preferably about 20 $\mu$l) and the suspension is incubated at a temperature and time sufficient to digest substantially all of the protein in the sample (Preferably, the suspension is incubated at 55° C. for at least 30 minutes). Afterwards, to disrupt the *Cryptosporidium parvum* oocysts, one or more freeze-thaw cycles are performed. In a preferred embodiment, 4 freeze-thaw cycles are performed. Each freeze-thaw cycle consists of freezing the suspension in a dry ice-acetone bath for a time suitable to solidify the suspension (preferably, 2 minutes) followed by thawing the solidified suspension in a 37° C. waterbath (preferably, for 2 minutes). After the last freeze-thaw, the suspension is centrifuged at about 15,000 rpm for 3 minutes in a microcentrifuge to pellet the debris. The supernatant fraction is collected and about 200 $\mu$l of AL buffer (Qiagen, Inc.) is added. The resulting sample is mixed thoroughly by vortexing and incubated for about 10 minutes at 70° C. Afterwards, about 200 μl of 95% ethanol is added and the mixture is mixed thoroughly by vortexing.

The nucleic acids in the mixture are isolated using a DNEASY minicolumn (Qiagen, Inc.) according to the procedure in the DNEASY Tissue Kit Handbook supra as follows. The mixture is transferred to a DNEASY minicolumn sitting in a collection tube, which is then centrifuged at about 8,000 rpm in a microcentrifuge for a minute. Afterwards, the minicolumn flow-through and collection tube are discarded and the minicolumn is placed in a second collection tube. Five hundred μl of AW1 buffer (Qiagen, Inc.) is added to the minicolumn and the minicolumn centrifuged at about 8,000 rpm for a minute. Afterwards, the minicolumn flow-through and second collection tube are discarded and the minicolumn is placed in a third collection tube. Five hundred μl of AW2 buffer (Qiagen, Inc.) is added and the minicolumn is centrifuged for several minutes at full speed to dry the minicolumn membrane. Afterwards, the minicolumn flow-through and third collection tube are discarded and the minicolumn is placed in a microcentrifuge tube. One hundred μl of AE buffer (Qiagen, Inc.) is added to elute the nucleic acids from the minicolumn. After a minute at room temperature, the minicolumn is centrifuged at about 8,000 rpm for a minute and the eluted nucleic acids are transferred to a microcentrifuge tube.

The multiplex reaction is performed in a single tube that combines the reverse transcription step to make cDNA copies of the bovine rotavirus and bovine coronavirus RNA genomes with a PCR step to amplify a target sequence in the resulting cDNAs and the *Cryptosporidium parvum* DNA genome. While the present invention can be performed using any one of a variety of RT-PCR/PCR protocols, the preferred embodiment of the present invention uses the Qiagen ONESTEP RT-PCR Kit (Qiagen, Inc.).

In the preferred embodiment, the following sets of primers are used in the multiplex RT-PCR/PCR assay. A *Cryptosporidium parvum* primer pair consisting of an upstream 5'-GCGAAGATGACCTTTTGATTTG-3' (SEQ ID NO: 1) primer and a downstream 5'-AGGATTTCTTCTTCTGAGGTTCC-3' (SEQ ID NO:2) primer wherein the primer pair amplifies a 194 bp DNA target sequence of the *Cryptosporidium parvum* genome as described in Balatbat et al., J. Clin. Microbiol. 34: 1769–1772 (1996). A bovine coronavirus primer pair consisting of an upstream 5'-CCGATCAGTCCGACCAATC-3' (SEQ ID NO:3) primer and a downstream 5'-AGAATGTCAGCC-GGGGTAT-3' (SEQ ID NO:4) primer wherein the primer pair amplifies a 406 bp target sequence of the nucleic acid sequence encoding the nucleocapsid gene as described in Tsunemitsu et al., Arch. Virol. 144: 167–175 (1999). The upstream SEQ ID NO:3 primer was modified from the 20-mer primer disclosed in Tsunemitsu et al. by omitting the G residue at the primer's 5' end. A bovine rotavirus primer pair consisting of an upstream 5'-ACCACCAAAT-ATGACACCAGC-3' (SEQ ID NO:5) primer and a downstream 5'-CATGCTTCTAATGGAAGCCAC-3' (SEQ ID NO:6) primer wherein the primer pair amplifies a 294 bp target sequence of the nucleic acid sequence encoding the VP6 protein identified from the nucleotide sequence from bovine rotavirus having GenBank Accession No. X53667 and which was submitted by Tarlow and McCrae. An *Escherichia coli* K99 primer pair that amplifies a 314 bp target sequence that encodes K99 pili, which can be used in the present invention, consists of upstream primer 5'-TATTATCTTAGGTGGTATGG-3' (SEQ ID NO:7) and downstream primer 5'-GGTATCCTTTAGC-AGCAGTATTTC-3 (SEQ ID NO:8) (Franck et al., J. Clin. Microbiol. 36: 1795–1797 (1998)). An *Escherichia coli* primer pair that amplifies a 190 bp target sequence that encodes heat-stable enterotoxin STa, which can be used in the present invention, consists of upstream primer 5'-GCTAATGTTGGCAATTTTTTATTTCTGTA-3' (SEQ ID NO:9) and downstream primer 5-AGGATTAC-AACAAAGTTCACAGCAGTAA-3' (SEQ ID NO:10) (Franck et al., ibid.).

To perform the multiplex RT-PCR/PCR, an aliquot of the aforementioned isolated nucleic acids is mixed with the above primer pairs to produce a reaction mixture. Preferably, the amount of each primer added is that amount that will provide a final PCR reaction concentration of 0.6 μM of each *Cryptosporidium parvum* primer; 0.9 μM of each bovine coronavirus primer; and 0.6 μM of each bovine rotavirus primer. When the *Escherichia coli* primer pairs for K99 or STa are included in the reaction, they are each at a concentration of about 0.5 μM. The above concentrations of primers enable relatively equal amplification of each PCR product. Thus, a master mix containing the above primers, the four deoxynucleotides triphosphates: adenosine deoxynucleotide triphosphate (dATP), guanosine deoxynucleotide triphosphate (dGTP), cytosine deoxynucleotide triphosphate (dCTP), and thymidine deoxynucleotide triphosphate (dTTP) or analogs thereof, and Qiagen ONESTEP PCR buffer (Qiagen, Inc.) is mixed with the extracted nucleic acids to make a final volume of 48 μl. The reaction mixture containing the nucleic acids is exposed to a denaturing step to denature the double-stranded RNA bovine rotavirus genome. Preferably, the reaction mixture is heated for 4 minutes at 95° C., cooled to 4° C., and then chilled on ice.

To perform the multiplex RT-PCR/PCR reaction, 2 μl of enzyme mix (Qiagen, Inc.) is added to the chilled reaction to bring the final reaction volume to 50 μl. The enzyme mix contains OMNISCRIPT reverse transcriptase, SENSISCRIPT reverse transcriptase, and HOTSTARTAQ DNA polymerase. The above enzymes are proprietary enzymes available from Qiagen, Inc. and are used as directed by the manufacturer. Preferably, the final concentration of the deoxynucleotide triphosphates in the reaction is 0.4 mM, the $Mg^{2+}$ is 2.5 mM, and the primer pair concentrations is as above.

In a first step, cDNA synthesis is performed at 50° C. for about 30 minutes which is followed by heating the reaction mixture at 95° C. for 15 minutes. The cDNA synthesis step makes cDNA copies of the rotavirus and coronavirus RNA genomes using their respective primer pairs. In the second step, the sample is subjected to about 44 cycles of PCR amplification. Each cycle consists of the following steps: 30 seconds at 94° C., 30 seconds at 55° C., and 1 minute at 72° C. Optionally, after the last cycle, an extension step is performed at 72° C. for 10 minutes, which is to ensure that most of the amplified DNA molecules have flush ends. In a preferred embodiment, after heating the cDNA synthesis reaction at 95° C. for 15 minutes, the reaction immediately enters into the PCR reaction. A suitable apparatus for performing the RT-PCR/PCR is the GENEAMP PCR System 2400 (Perkin-Elmer, Foster City, Calif.).

After the above reaction, the amplified PCR reaction products are separated by agarose gel electrophoresis on 2% agarose gels. The amplified products are visualized by staining the gels with an indicator for aiding the visualization of DNA on agarose gels, e.g., ethidium bromide, acridine orange, and SYBOR Green or Gold (Molecular Probes, Eugene, Oreg.). When the reaction contains the above *Escherichia coli* K99 primers or the STa primers, the PCR product produced by the K99 primer is very close in size to the bovine rotavirus PCR product (314 bp and 294 bp, respectively) and the PCR product produced by the STa primer is very close in size to the *Cryptosporidium parvum* PCR product (190 bp and 194 bp, respectively). Therefore, it can be difficult to resolve the PCR products by agarose gel electrophoresis. To be able to distinguish the PCR products it can be desirable to perform side-by-side PCR reactions wherein a first reaction comprises the primers for detecting bovine coronavirus, bovine rotavirus, and *Cryptosporidium parvum* and a second reaction comprises the primers for detecting *Escherichia coli* K99 and STa. Other combinations of primers can also be used. For example, in a first reaction, the primers comprise the primers for *Escherichia coli* K99, STa, and bovine coronavirus, and in a second reaction, the primers comprise the primers for bovine rotavirus and *Cryptosporidium parvum*. It would be readily apparent to one skilled in the art that other primer combinations could be used as well.

Alternatively, the multiplex RT-PCR/PCR reaction can contain all of the above primers and the PCR products are resolved on a polyacrylamide gel or by capillary electrophoresis, which enables all of the PCR products to be resolved with little difficulty. In a desirable embodiment of the multiplex RT-PCR/PCR method, the PCR products are detected by a means that does not depend on resolving the PCR products based upon size. Such means include DNA array or microchip technology, which uses hybridization to DNA immobilized on a substrate to detect the PCR products, and real-time PCR technology, which measures fluorescence released or quenched during the PCR reaction to detect the PCR products.

The multiplex RT-PCR/PCR method of the present invention for detecting bovine coronavirus, bovine rotavirus, and *Cryptosporidium parvum* was compared to current diagnostic tests for detecting these pathogens. The present invention detected 11 out of 12 samples containing bovine rotavirus nucleic acids whereas the conventional methods of FA, electron microscopy, and ELISA detected only 6 out of 12. The present invention detected 10 out of 12 samples containing *Cryptosporidium parvum* whereas the conventional method of staining detected only 5 out of 12. The present invention detected 5 out of 12 samples containing bovine coronavirus which was similar to the conventional methods of FA and electron microscopy which detected 5 out of 12. Thus, the multiplex RT-PCR/PCR method of the present invention is more sensitive for detecting the above pathogens than current methods.

Figure 2:
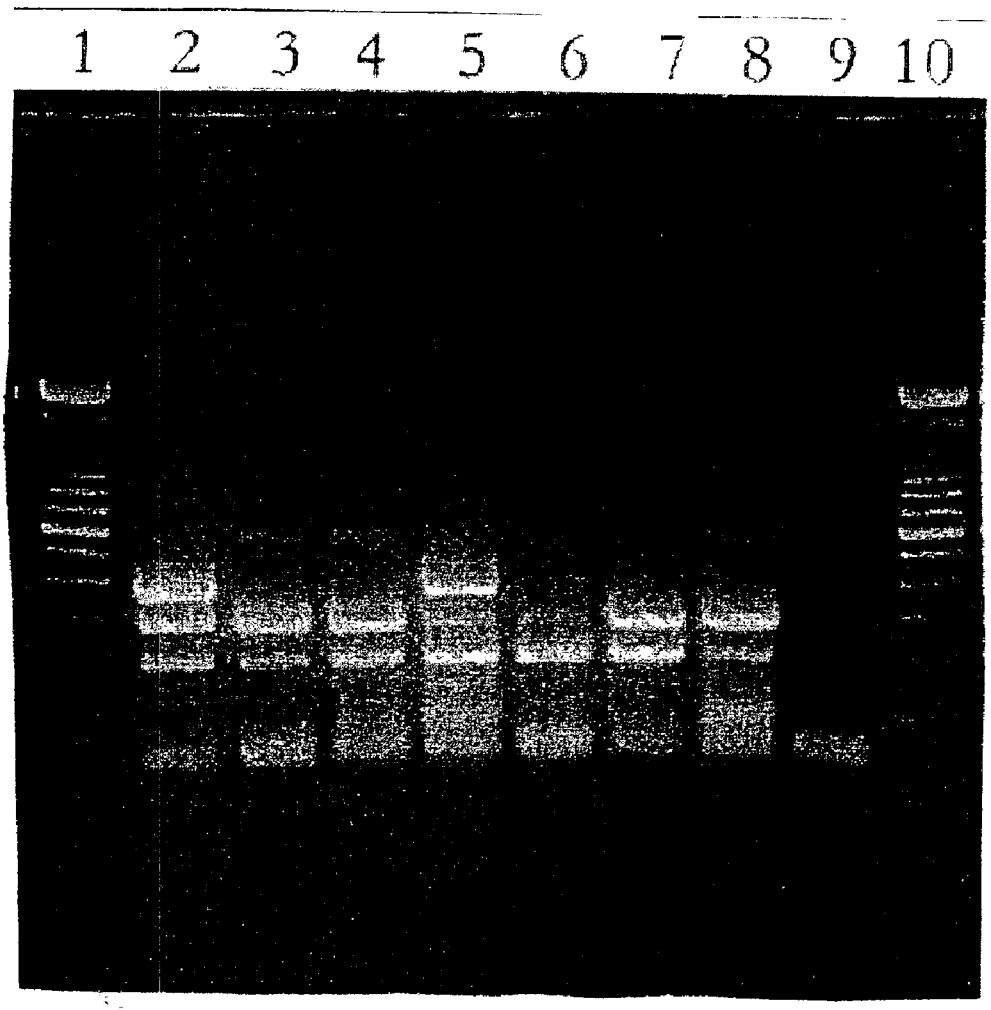
FIG. 2 shows the PCR amplification products resolved on an ethidium bromide stained 2% agarose gel following the multiplex RT-PCR/PCR reaction of the present invention on nucleic acids extracted from fecal samples submitted to the Animal Health Diagnostic Laboratory at Michigan State University. Lanes 1 and 10 show a 100 base-pair (bp) DNA ladder. Lane 2 shows a positive control from reference strains of bovine coronavirus, bovine rotavirus, and *Cryptosporidium parvum* showing the 406 bp, 294 bp, and 194 bp PCR products, respectively. Lane 9 shows a negative control using water as the template. Lanes 3–8 show the PCR products obtained from the submitted fecal samples.

The detection limit or sensitivity for each of the above pathogens was determined initially by testing in serial ten-fold dilutions of reference preparations of the above pathogens with the primer pairs used in the multiplex RT-PCR/PCR of the present invention. For each pathogen, the reaction mixture contained the particular template for the pathogen and each of the above primer pairs for bovine rotavirus, bovine coronavirus, and *Cryptosporidium parvum*. The detection limits were 1 $TCID_{50}$ for rotavirus, 0.1 $TCID_{50}$ for coronavirus, and 10 oocysts for *Cryptosporidium parvum*. The multiplex RT-PCR/PCR of the present invention was validated using field samples from calves having diarrhea. The results of the validation are shown in FIGS. 1 and 2.

As discussed above, because the 314 bp *Escherichia coli* K99 PCR product is close in size to the 294 bp bovine rotavirus PCR product and the 190 bp *Escherichia coli* STa PCR product is close in size to the 194 bp *Cryptosporidium parvum* PCR product, it can be difficult to resolve the above PCR products on agarose gels. However, the present invention is not limited to agarose gels, the PCR products can be resolved by polyacrylamide gel electrophoresis, capillary electrophoresis, and by means that do not rely on resolving the PCR products based upon size. For example, a method and detection system that is particularly useful is the real-time PCR-based TAQMAN technology (Heid et al., Genome Res. 6: 986–994 (1996)) or other real-time PCR-based technology. TAQMAN is a registered trademark of Roche Molecular Systems, Inc. (Alameda, Calif.). Methods and apparatus for performing TAQMAN-based reactions and detecting the reaction products are available from Applied Biosystems Division, Perkin-Elmer, Foster City, Calif.

The TAQMAN technology does not rely upon resolving the PCR products based upon size. Instead, it employs energy transfer donor-acceptor fluorophore technology and uses an apparatus to detect fluorescence produced by the energy transfer donor fluorophore during the PCR reaction. Therefore, the TAQMAN technology allows for the rapid and real-time detection and enumeration of target sequences during the PCR reaction. Thus, the TAQMAN technology provides a means for characterizing PCR products without the need for gel electrophoresis following the PCR reaction. Therefore, using the oligonucleotide primers disclosed herein for bovine coronavirus, bovine rotavirus, *Cryptosporidium parvum*, and *Escherichia coli* producing K99 pili or heat-stable enterotoxin STa or STb and the appropriately labeled oligonucleotide probes, wherein each probe is complementary to a particular sequence within the target sequence, the multiplex RT-PCR/PCR method present invention provides a means not only for real-time detection and identification of bovine coronavirus, bovine rotavirus, *Cryptosporidium parvum*, and *Escherichia coli* producing K99 pili or heat-stable enterotoxin STa or STb in a fecal sample, but also a real-time means for enumerating or quantifying the number of each of these pathogens in the sample.

Each probe that is used in the multiplex RT-PCR/PCR method of the present invention is a dual-labeled oligonucleotide probe that is complimentary to a sequence within the target sequence downstream from either the upstream or downstream primer. Preferably, the oligonucleotide probe is about 10 nucleotides in length and is complimentary to a sequence less than 100 nucleotides from either the upstream or downstream primer. Each dual-labeled oligonucleotide probe is labeled at the 5' end with an energy transfer donor moiety and at the 3' end with an energy transfer acceptor moiety. In particular, the moieties on the dual-labeled probe are fluorophores, wherein the fluorescent energy of the donor fluorophore is absorbed by an acceptor fluorophore that is in close proximity to the donor. U.S. Pat. No. 5,866,336 to Nazarenko et al., discloses particular molecular energy transfer fluorophores and methods for their use in oligonucleotide primers in nucleic amplification methods. Common fluorophores suitable for use as donor-acceptor pairs in the present invention are fluorescein, 5-carboxyfluorescein (FAM), 2'7'-dimethoxy-4',5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), tetrachloro-6-carboxy-fluorescein (TET), VIC (Perkin-Elmer Biosystems), and 5-(2'-aminoethyl) aminonaphthalene-1-sulfonic acid (EDANS). Whether a fluorophore is an acceptor or a donor is defined by its excitation and emission spectra. For example, FAM is a suitable donor fluorophore for use with JOE, TAMRA, and ROX which quenches the fluorescence of the donor. In a preferred embodiment, the dual-labeled oligonucleotide probe is labeled at the 5' end with a donor fluorophore such as FAM, TET, or VIC and at the 3' end with an acceptor or quenching fluorophore such as TAMRA. Therefore, in the multiplex RT-PCR/PCR assay of the present invention, the probe specific to a region of the target sequence flanked by SEQ ID NO:1 and SEQ ID NO:2 is labeled at the 5' end with FAM and the 3' end with TAMRA, the probe specific to a region of the target sequence flanked by SEQ ID NO:3 and SEQ ID NO:4 is labeled at the 5' end with TET and the 3' end with TAMRA, and the probe specific to a region of the target sequence flanked by SEQ ID NO:5 and SEQ ID NO:6 is labeled at the 5' end with VIC and the 3' end with TAMRA. Other donor-acceptor combinations would be readily apparent to one skilled in the art.

The use of dual-labeled oligonucleotide probes in PCR reactions is disclosed in U.S. Pat. No. 5,716,784 to DiCesare. In the PCR step of the multiplex RT-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction. An apparatus suitable for detection is the ABI Prism 7700 sequence detector using 96-well reaction plates or GENE-AMP PC System 9600 or 9700 in 9600 emulation mode followed by analysis in the ABA Prism Sequence Detector or TAQMAN LS-50B PCR Detection System. The above are available from Perkin-Elmer Applied Biosystems. The present invention can also be performed in other real-time PCR systems with multiplexing capabilities. The amount of detected fluorescence is proportional to the amount of fluorescent product released. To prevent extension from the 3' end of the dual-labeled probe by the Taq polymerase, the 3' end of the probe is phosphorylated.

Another method for detecting PCR products that does not rely upon resolving the PCR products based upon size is the DNA array or biochip technology. The DNA array technology can be used for detecting the amplified PCR products from bovine coronavirus, bovine rotavirus, *Cryptosporidium parvum*, and *Escherichia coli* producing K99 pili or heat-stable enterotoxin STa or STb produced using the multiplex RT-PCR/PCR method of the present invention. In general, a DNA array is prepared comprising the DNA complementary to the PCR products for bovine coronavirus, bovine rotavirus, *Cryptosporidium parvum*, *Escherichia coli* producing K99 pili, and *Escherichia coli* producing heat-stable enterotoxin STa or STb wherein the DNA is immobilized in an array on a substrate such as a silicon chip. Preferably, the DNA for each pathogen is separately immobilized on the substrate. The immobilized DNA can be denatured double-stranded DNA or can be a single-stranded DNA. Preferably, the DNA is prepared using a DNA synthesizer.

In general, using the DNA array for detecting the PCR products is as follows. A multiplex RT-PCR/PCR reaction as taught herein is performed on a fecal sample. For detecting the PCR products, an aliquot of the reaction is incubated with the DNA array in a hybridization reaction. Any PCR product produced in the reaction that is complementary to the immobilized DNA will hybridize to the immobilized DNA, which indicates that the fecal sample contains the pathogen corresponding to the immobilized DNA. Detection of the hybridized PCR product can be by methods well known in the art, which includes, but is not limited to, labeling the PCR products with a fluorescence group, labeling the PCR products with a radioactive isotope, electron transfer reactions from the DNA to the substrate, and mass spectrometry. Other detection methods include methods such as alkaline phosphatase-based and horseradish peroxidase detection methods that produce a colorimetric product, or luminescence-based methods that produce light. The following U.S. Patents disclose methods for producing DNA arrays that can be used with the multiplex RT-PCR/PCR method of the present invention: U.S. Pat. No. 6,136,962; U.S. Patent Pat. No. 6,127,129; U.S. Pat. No. 6,110,426; U.S. Pat. No. 6,090,555; U.S. Pat. No. 6,083,697; U.S. Pat. No. 6,051,380; U.S. Pat. No. 6,030,782; U.S. Pat. No. 6,027,890; U.S. Pat. No. 6,027,889; U.S. Pat. No. 6,027,880; U.S. Pat. No. 6,017,696; U.S. Pat. No. 5,919,208; U.S. Pat. No. 5,874,219; U.S. Pat. No. 5,861,242; U.S. Pat. No. 5,856,101; U.S. Pat. No. 5,843,651; U.S. Pat. No. 5,837,860; U.S. Pat. No. 5,837,832; U.S. Pat. No. 5,807,522; U.S. Pat. No. 5,688,642; U.S. Pat. No. 5,633,724; U.S. Pat. No. 5,599,668; and, U.S. Pat. No. 5,593,839.

In an embodiment further still of the present invention, the fecal sample is subjected to an immunomagnetic separation step in which magnetic beads coated with antibodies against bovine coronavirus, bovine rotavirus, *Cryptosporidium parvum*, and *Escherichia coli* producing K99 pili or heat-stable enterotoxin STa or STb are used to collect the pathogens from the environmental sample free of other organisms and inhibitors. The antibodies can be polyclonal antibodies or monoclonal antibodies. The immunomagnetic separation step is useful for concentrating the bovine coronavirus, bovine rotavirus, *Cryptosporidium parvum*, and *Escherichia coli* producing K99 pili or heat-stable enterotoxin STa or STb in a sample, particularly when the concentration would otherwise be insufficient to provide sufficient nucleic acids for the multiplex RT-PCR/PCR analysis. Because one or more of the above pathogens may be at a level which is undetectable by PCR, the immunomagnetic separation step increases the probability that all of the above four pathogens will be detected by the multiplex RT-PCR/PCR assay.

In general, antibodies which are specific for bovine coronavirus, bovine rotavirus, *Cryptosporidium parvum*, and *Escherichia coli* producing K99 pili or heat-stable enterotoxin STa or STb are attached to super-paramagnetic mono-sized polymer particles to make immunomagnetic beads. The immunomagnetic beads are mixed with the fecal sample, which may be diluted in water or suitable buffer, and the immunomagnetic beads, which become complexed with bovine coronavirus, bovine rotavirus, *Cryptosporidium parvum*, and *Escherichia coli* producing K99 pili or heat-stable enterotoxin STa or STb in the sample, are separated from the sample by a magnetic field. There are two ways to separate bovine coronavirus, bovine rotavirus, *Cryptosporidium parvum*, and *Escherichia coli* producing K99 pili or heat-stable enterotoxin STa or STb using immunomagnetic separation, positive isolation and negative isolation.

In the positive isolation embodiment, the paramagnetic beads are coated with antibodies against bovine coronavirus, bovine rotavirus, *Cryptosporidium parvum*, and *Escherichia coli* producing K99 pili or heat-stable enterotoxin STa or STb and the coated beads mixed with the fecal sample. The beads complex with the bovine coronavirus, bovine rotavirus, *Cryptosporidium parvum*, and *Escherichia coli* producing K99 or enterotoxin STa or STb in the sample, and are removed by a magnetic field. In an indirect embodiment of the positive isolation embodiment, the antibodies against the bovine coronavirus, bovine rotavirus, *Cryptosporidium parvum*, and *Escherichia coli* producing K99 or enterotoxin STa or STb pathogens are mixed with the sample wherein the antibodies bind the pathogens in the sample to form a first complex. The first complex is separated from the sample by adding to the mixture paramagnetic beads coated with an antibody against the antibodies against the pathogens, e.g., the antibodies against the pathogens are mouse antibodies and the antibodies on the beads are anti-mouse antibody IgG. The immunomagnetic beads binds the first complex forming a second complex which is separated from the sample by a magnetic field. The bovine coronavirus, bovine rotavirus, *Cryptosporidium parvum*, and *Escherichia coli* are eluted from the immunomagnetic beads in sterile water and analyzed as taught herein.

In a negative isolation embodiment, unwanted organisms are removed from the sample by providing a cocktail comprising antibodies against a variety of unwanted organisms. In a reaction, antibodies in the cocktail are allowed to bind to the unwanted organisms in the sample. Next, the immunomagnetic beads coated with an antibody against the antibodies in the cocktail are added which binds all of the antibodies, including those bound to the unwanted organisms. The bound organisms are separated by a magnetic field. The bovine coronavirus, bovine rotavirus, *Cryptosporidium parvum*, and *Escherichia coli* producing K99 or enterotoxin STa or STb, which remains in the sample, are analyzed as taught herein.

Preferably, the immunomagnetic separation uses the positive isolation method and the antibodies against bovine coronavirus, bovine rotavirus, *Cryptosporidium parvum*, and *Escherichia coli* producing K99 pili or heat-stable enterotoxin STa or STb are monoclonal antibodies. Immunomagnetic beads containing anti-mouse IgG are resuspended thoroughly in the vial and the desired amount of beads transferred to a tube. Preferably, 25 µl of 107 beads per ml is transferred to each of four tubes. The tubes are placed in a magnetic block and the fluid is removed. The IgG-beads are washed twice with washing buffer (phosphate buffered saline (PBS) containing 1% bovine serum albumen (BSA)). Next, each tube of IgG-beads is incubated with mouse monoclonal antibodies against one of bovine coronavirus, bovine rotavirus, *Cryptosporidium parvum*, and *Escherichia coli* in washing buffer at about 1 µg of antibodies for every 107 beads. Therefore, 4 tubes are set-up, each containing antibodies against one of bovine coronavirus, bovine rotavirus, *Cryptosporidium parvum*, and *Escherichia coli* producing K99 or enterotoxin STa or STb. The antibodies are bound to the IgG-beads by incubating for about 2 hours at 4° C. with gentle mixing. Afterwards, the tubes containing the antibody bound to the IgG-beads are placed in a magnetic block and washed twice with washing buffer. The antibody bound IgG-beads are resuspended in about 25 µl of washing buffer. Afterwards, the antibody bound IgG-beads from each of the 4 tubes are combined to produce a mixture containing any ratio of IgG-beads bound to antibodies against bovine coronavirus, bovine rotavirus, *Cryptosporidium parvum*, and *Escherichia coli* producing K99 or enterotoxin STa or STb that is desired.

A fecal sample is cooled and added to the above antibody bound IgG-bead mixture, and incubated for about 1 hour at 4° C. with gentle mixing to bind any bovine coronavirus, bovine rotavirus, *Cryptosporidium parvum*, and *Escherichia coli* producing K99 pili or heat-stable enterotoxin STa or STb, which may be in the sample. Afterwards, the tube is placed in a magnetic block for about 2 minutes to allow separation. The fluid is removed, the antibody bound IgG-beads removed from the magnetic block and washed with washing buffer. The tube is returned to the magnetic block and after about 1 minute, the fluid is removed. The washing is repeated at least once. Then, any bound bovine coronavirus, bovine rotavirus, *Cryptosporidium parvum*, and *Escherichia coli* is eluted from the beads with sterile water. Afterwards, the tube is placed in the magnetic block and the sterile water containing the bovine coronavirus, bovine rotavirus, *Cryptosporidium parvum*, and *Escherichia coli* are transferred to another tube and analyzed according to the multiplex RT-PCR/PCR detection method of the present invention.

The following examples are intended to promote a further understanding of the present invention.

EXAMPLE 1

This example shows a method for recovering nucleic acids from feces. Both RNA and DNA were simultaneously extracted from 12 fecal specimens from calves with diarrhea submitted to the Animal Health Diagnostic Laboratory at Michigan State University using the Qiagen DNEASY Tissue Kit following the DNEASY protocol for animal tissues in the DNEASY Tissue Kit Handbook (Qiagen, Inc., April 1999 Edition, pp. 16–18) provided by the manufacturer as modified below.

About 20 to 30 mg of feces were resuspended in 180 µl ATL buffer (Qiagen, Inc.). To lyse the cells in the suspension, 20 µl of proteinase K was added and the suspension was incubated for 30 minutes at 55° C. Afterwards, to disrupt the *C. parvum* oocysts, four freeze-thaw cycles were performed. Each freeze-thaw cycle consisted of freezing the suspension in a dry ice-acetone bath for 2 minutes followed by thawing in a 37° C. waterbath for another 2 minutes. After the last freeze-thaw, the suspension was centrifuged at 15,000 rpm for 3 minutes to pellet the debris. The supernatant fraction was collected and 200 µl of AL buffer (Qiagen, Inc.) was added. The resulting sample was mixed thoroughly by vortexing and incubated at 70° C. for 10 minutes. Afterwards, 200 µl of 95% or greater ethanol was added and the mixture was mixed thoroughly by vortexing.

Then, the mixture was transferred to a DNEASY minicolumn (available from Qiagen, Inc.) sitting in a 2 ml collection tube, which was then centrifuged at 6,000 x g (about 8,000 rpm) for 1 minute. Afterwards, the minicolumn flow-through and collection tube were discarded and the minicolumn was placed in a second 2 ml collection tube. Five hundred µl of AW1 buffer (Qiagen, Inc.) was added and the minicolumn centrifuged at 8,000 rpm for 1 minute. Afterwards, the minicolumn flow-through and second collection tube were discarded and the minicolumn was placed in a third 2 ml collection tube. Five hundred µl of AW2 buffer (Qiagen, Inc.) was added and the minicolumn was centrifuged for 3 minutes at full speed (15,000 rpm) to dry the minicolumn membrane. Afterwards, the minicolumn flow-through and third collection tube were discarded and the minicolumn was placed in a microcentrifuge tube. One hundred μl of AE buffer (Qiagen, Inc.) was added to elute the nucleic acids from the minicolumn. After 1 minute at room temperature, the minicolumn was centrifuged at 8,000 rpm for 1 minute and the eluted nucleic acids were transferred to a microcentrifuge tube to produce the nucleic acid sample for the multiplex RT-PCR/PCR in Example 2.

EXAMPLE 2

This example shows the multiplex RT-PCR/PCR assay of the present invention using the nucleic acids isolated in Example 1 to detect bovine corona virus, bovine rotavirus, and *Cryptosporidium parvum*.

A single reaction tube was used for the multiplex reaction of each nucleic acid sample from Example 1. In this example, 12 separate multiplex reactions were performed.

The multiplex reactions were performed using the Qiagen ONESTEP RT-PCR Kit in a final reaction volume of 50 μl with the following final primer concentrations. The amount of each primer was as follows: 0.6 μM of each *Cryptosporidium parvum* primer (SEQ ID NO:1 and SEQ ID NO:2); 0.9 μM of each bovine coronavirus primer (SEQ ID NO:3 and SEQ ID NO:4); and, 0.6 μM of each bovine rotavirus primer (SEQ ID NO:5 and SEQ ID NO:6).

Prior to performing the PCR step of the reaction, i.e., before adding the enzyme mix, the samples containing the nucleic acids were exposed to a denaturing step to denature the double-stranded RNA bovine rotavirus genome. Thus, 3 μl of the nucleic acid sample was transferred to a 0.2 ml PCR tube and the three sets of primer pairs (added in their proper volumes to obtain the appropriate concentrations at the final PCR volume of 50 μl as described above) were mixed together with RNase-free water and master mix to a volume of 48 μl and denatured for 4 minutes at 95° C., then cooled to 4° C. in a separate program in a thermocycler (GENEAMP PCR System 2400, Perkin-Elmer).

The tube was then chilled on ice and 2 μl of the enzyme mix, which contained OMNISCRIPT reverse transcriptase, SENSISCRIPT reverse transcriptase, and HOTSTARTAQ DNA polymerase, was added resulting in a final volume of 50 μl. Next, to perform the multiplex reaction, the following conditions were used in the thermocycler. The cDNA synthesis was performed at 50° C. for 30 minutes; followed by pre-denaturation at 95° C. for 15 minutes; followed by 44 cycles of PCR amplification wherein each cycle consisted of 30 seconds at 94° C., 30 seconds at 55° C., and 1 minute at 72° C. After the last cycle, an extension step was performed at 72° C. for 10 minutes.

The amplified PCR reaction products were separated by agarose gel electrophoresis on 2% agarose gels in Tris-acetate-EDTA (TAE) buffer at 200 volts for about 40 minutes. About 40 μl of the PCR reaction mixture was electrophoresed. Afterwards, the amplified products, which had been separated by electrophoresis, were visualized by staining the gels with an ethidium bromide solution and viewing the products by ultraviolet light using a UV transilluminator. Optionally, the agarose gel contains 0.5 μg/ml ethidium bromide.

The multiplex PCR results shown in FIGS. 1 and 2 demonstrate that the present invention enables the simultaneous detection of bovine rotavirus, bovine coronavirus, and *Cryptosporidium parvum* in a fecal samples. In each Figure, lanes 1 and 10 show the DNA molecular weight DNA markers, lane 2 shows a positive control containing nucleic acids from bovine rotavirus, bovine coronavirus, and *Cryptosporidium parvum*, and lane 9 shows a negative control that contained no nucleic acids. Lane 2 shows the expected 406 bp, 294 bp, and 194 bp products multiplex PCR products, which corresponded to the multiplex PCR products expected for bovine coronavirus, bovine rotavirus, and *Cryptosporidium parvum*, respectively.

In FIG. 1, lane 3 shows the PCR products from a fecal that contained only nucleic acids from a calf infected with *Cryptosporidium parvum*. Lanes 4 and 7 show the PCR products from a fecal sample that contained nucleic acids from a calf infected with bovine rotavirus and *Cryptosporidium parvum*. Lanes 5 and 6 show the PCR products from a fecal sample that contained nucleic acids from a calf infected with bovine rotavirus and bovine coronavirus. Lane 8 shows that the fecal sample contained nucleic acids from all three pathogens indicating that the calf was infected with all three pathogens.

In FIG. 2, lanes 3, 4, 7, and 8 show that the fecal samples contained nucleic acids from calves infected with bovine rotavirus and *Cryptosporidium parvum*. Lane 5 shows that the calf was infected with bovine coronavirus, bovine rotavirus, and *Cryptosporidium parvum*. Lane 6 shows that the calf was also infected with *Cryptosporidium parvum*, bovine rotavirus, and bovine coronavirus. The bovine coronavirus band was very weak but detectable.

EXAMPLE 3

This example illustrates separation of bovine coronavirus, bovine rotavirus, *Cryptosporidium parvum*, and *Escherichia coli* K99 from a fecal sample.

Dynabeads pan mouse IgG (Dynal, Inc. #110.21) are resuspended thoroughly in their storage vial. Four tubes are set up and to each of the tubes, 25 μl of 10⁷ beads per ml is transferred. The tubes are placed in a magnetic block (Home Depot) and the fluid is removed. The beads are washed twice with washing buffer (phosphate buffered saline (PBS) containing 1% bovine serum albumen (BSA)). Next, for each tube, the beads are incubated with mouse monoclonal antibodies against one of bovine coronavirus, bovine rotavirus, *Cryptosporidium parvum*, or *Escherichia coli* K99 in washing buffer at 1 μg of antibodies for every 10⁷ beads. Thus, four tubes are prepared, each containing antibodies against one of the four pathogens. The antibodies are bound to the IgG on the beads by incubating for 2 hours at 4° C. with gentle mixing using a mixing device from Tamiya. Afterwards, the tube containing the IgG-antibody beads are placed in the magnetic block and washed twice with washing buffer. For each wash the beads are gently resuspended in the washing buffer and then concentrated using the magnetic block. The beads are resuspended in 25 μl of washing buffer. Afterwards, the IgG-antibody beads are pooled in any combination desired.

Fecal samples are diluted as in Example 1. Each sample is cooled to 4° C. and then mixed with a mixture containing each of the above IgG-antibody coated beads in a tube and incubated for 1 hour at 4° C. with gentle mixing on the mixing device. Afterwards, the tube is placed in a magnetic block for about 2 minutes to allow separation. The fluid is removed, the antibody bound IgG-beads removed from the magnetic block and washed with washing buffer. The tube is returned to the magnetic block and after about 1 minute, the fluid is removed. The washing is repeated at least once. Then, the bound bovine coronavirus, bovine rotavirus, *Cryptosporidium parvum*, and *Escherichia coli* K99 is eluted from the beads with sterile water. Afterwards, the tube is placed in the magnetic block and the sterile water containing the bovine coronavirus, bovine rotavirus, *Cryptosporidium parvum*, and *Escherichia coli* K99 are transferred to another tube and nucleic acids extracted and analyzed as shown in Example 2.

While the present invention is described herein with reference to illustrated embodiments, it should be understood that the invention is not limited hereto. Those having ordinary skill in the art and access to the teachings herein will recognize additional modifications and embodiments within the scope thereof. For example, the multiplex RT-PCR/PCR method of the present invention can further include one or more of the PCR primers which target the genes encoding the *Escherichia coli* STaP, STaH, and LT enterotoxins and K88, 987P, and F41 adhesins as disclosed in Mainil et al., Am. J. Vet. Res. 51: 187–190 (1990). Therefore, the present invention is limited only by the claims attached herein.

We claim:

1. A method of screening to simultaneously detect *Cryptosporidium parvum*, bovine coronavirus and bovine rotavirus in a calf fecal sample, the method comprising:

(a) providing a calf fecal sample;

(b) performing a freeze-thaw procedure for the disruption of *Cryptosporidium parvum* oocysts;

(c) performing a procedure for isolating nucleic acids consisting of single-stranded RNA of the bovine coronavirus, double-stranded RNA of the bovine rotavirus and DNA of the *Cryptosporidium parvum* from the calf fecal sample to provide an isolate;

(d) providing in an RT-PCR/PCR reaction mixture the isolate, a first oligonucleotide primer pair consisting of an upstream primer of SEQ ID NO: 1 and a downstream primer of SEQ ID NO: 2, which anneals to a first target nucleic acid sequence of *Cryptosporidium parvum*, a second oligonucleotide primer pair consisting of an upstream primer of SEQ ID NO: 3 and a downstream primer of SEQ ID NO: 4, which anneals to a second target nucleic acid sequence of bovine coronavirus, and third oligonucleotide primer pair consisting of an upstream primer of SEQ ID NO: 5 and a downstream primer of SEQ ID NO: 6, which anneals to a third target nucleic acid sequence of bovine rotavirus, wherein each primer pair flanks its respective target nucleic acid sequence for PCR amplification of the target nucleic acid, and four deoxynucleotide triphosphates selected from the group consisting of adenosine deoxynucleotide triphosphate, guanosine deoxynucleotide triphosphate, thymidine deoxynucleotide triphosphate, cytosine deoxynucleotide triphosphate, and nucleotide analogs thereof;

(e) denaturing the double-stranded RNA of the bovine rotavirus to provide denatured double-stranded RNA;

(f) providing a thermostable DNA polymerase, and a reverse transcriptase;

(g) synthesizing bovine coronavirus cDNA from the single-stranded RNA of the bovine coronavirus, and bovine rotavirus cDNA from the denatured double-stranded RNA of the bovine rotavirus under suitable reverse transcription reaction conditions with the deoxynucleotide triphosphates and reverse transcriptase;

(h) amplifying by a PCR reaction the first target nucleic acid from the DNA of the *Cryptosporidium parvum*, the second target nucleic acid from the bovine coronavirus cDNA, and the third target nucleic acid from the bovine rotavirus cDNA in the reaction mixture under suitable PCR reaction mixture temperature conditions by a repetitive series of PCR thermal cycling steps comprising:

(1) denaturing the DNA and cDNA into denatured strands;

(2) annealing the oligonucleotide primers provided in step (d) to the denatured strands of the DNA and cDNA, and (3) extending the hybridized primers with the four deoxynucleotide triphosphates and the nucleic acid polymerase to provide amplified PCR products; and (i) following amplification, screening for the first, second, and third target nucleic acids in the amplified PCR products so as to simultaneously detect the *Cryptosporidium parvum*, bovine coronavirus and bovine rotavirus, respectively, in the calf fecal sample.

2. The method of claim 1 wherein the reaction mixture comprises 0.6 μM of each of the upstream primer and the downstream primer of the first primer pair, 0.9 μM of each of the upstream primer and the downstream primer of the second primer pair, and 0.6 μM each of the upstream primer and the downstream primer of the third primer pair.

3. The method of claim 1 wherein the bovine coronavirus cDNA and the bovine rotavirus cDNA is synthesized in a reaction at about 50° C. for about 30 minutes followed by predenaturation at 95° C. for 15 minutes.

4. The method of claim 1 wherein the PCR reaction is for 44 cycles wherein each cycle consists of denaturing at about 94° C. for about 30 seconds, annealing at 55° C. for about 30 seconds, and extending at about 72° C. for about 1 minute.

5. The method of claim 1 wherein primer pairs further include at least one oligonucleotide primer pair, which anneals to a target nucleic acid sequence of *Escherichia coli*, selected from the group of primer pairs consisting of an upstream primer consisting of SEQ ID NO: 7 and a downstream primer consisting of SEQ ID NO:8 for detecting a target sequence encoding K99 pili, and an upstream primer consisting of SEQ ID NO: 9 and a downstream primer consisting of SEQ ID NO: 10 for detecting a target encoding heat-stable enterotoxin STa.

6. The method of claim 1 or 5 wherein the sample comprises the bovine coronavirus, bovine rotavirus, *Cryptosporidium parvum*, and *Escherichia coli* K99 which are isolated from the calf fecal sample by immunomagnetic separation.

7. The method of claim 1 that includes one or more probes for detecting the amplified PCR product wherein each probe is complementary to a sequence within the target sequence of *Cryptosporidium parvum*, bovine coronavirus or bovine rotavirus.

8. The method of claim 7 wherein the probes are labeled at its 5' end with an energy transfer donor fluorophore and labeled at its 3' end with an energy transfer acceptor fluorophore.

9. The method of claim 8 wherein the fluorophore is selected from the group consisting of fluorescein, 5-carboxyfluorescein (FAM), 2'7'-dimethoxy-4',5'-dichloro-6-carboxyfluorescein (JOE), rhodamine, 6-carboxyrhodamine (R6G), N,N,N',N'-tetramethyl-6-carboxyrhodamine (TAMRA), 6-carboxy-x-rhodamine (ROX), 4-(4'-dimethylaminophenylazo) benzoic acid (DABCYL), tetrachloro-6-carboxy-fluorescein (TET), VIC, and 5-(2'-aminoethyl)aminonaphthalene-1-sulfonic acid (EDANS).

10. The method of claim 7 wherein the probes are blocked against chain extension at its 3' end.

* * * * *

UNITED STATES PATENT AND TRADEMARK OFFICE
CERTIFICATE OF CORRECTION

PATENT NO. : 6,867,021 B2
DATED : March 15, 2005
INVENTOR(S) : Roger K. Maes and Annabel G. Wise It is certified that error appears in the above-identified patent and that said Letters Patent is hereby corrected as shown below:

Column 15,
Lines 48 and 57, "107 beads" should be -- $10^7$ beads --.

Column 18,
Line 35, "10' beads" should be -- $10^7$ beads --.
Line 43, "107 beads" should be -- $10^7$ beads --.

Signed and Sealed this

Seventeenth Day of May, 2005

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:
      Crypstosporidium parvum upstream PCR primer

<400> SEQUENCE: 1
gcgaagatga ccttttgatt tg                                           22

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:
      Cryptosporidium parvum downstream PCR primer

<400> SEQUENCE: 2
aggatttctt cttctgaggt tcc                                          23

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Bovine
      coronavirus upstream PCR primer

<400> SEQUENCE: 3
ccgatcagtc cgaccaatc                                               19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Bovine
      coronavirus downstream PCR primer

<400> SEQUENCE: 4
agaatgtcag ccggggtat                                               19

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Bovine
      rotavirus upstream PCR primer

<400> SEQUENCE: 5
```

```
accaccaaat atgacaccag c                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Bovine
      rotavirus downstream PCR primer

<400> SEQUENCE: 6
catgcttcta atggaagcca c                                              21

<210> SEQ ID NO 7
<211> LENGTH: 20
<212> TYPE: DNA
<213> ORGANISM: Artificial Sequence
<220> FEATURE:
<223> OTHER INFORMATION: Description of Artifical Sequence: Escherichia
      coli K99 upstream PCR primer

<400> SEQUENCE: 7
tattatctta ggtggtatgg                                                20

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Escherichia
      coli K99 downstream PCR primer

<400> SEQUENCE: 8
ggtatccttt agcagcagta tttc                                           24

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Esherichia
      coli STa upstream PCR primer

<400> SEQUENCE: 9
gctaatgttg gcaatttta tttctgta                                        28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Escherichia
      coli STa downstream PCR primer

<400> SEQUENCE: 10
aggattacaa caaagttcac agcagtaa                                       28
```